United States Patent [19]

Shaw et al.

[11] 4,358,608

[45] Nov. 9, 1982

[54] PROCESS FOR PRODUCING UNSATURATED ALIPHATIC ACIDS

[75] Inventors: Wilfrid G. Shaw, Lyndhurst; David B. Terrill, Bedford; David R. Woodbury, Bedford Hts., all of Ohio

[73] Assignee: The Standard Oil Company, Cleveland, Ohio

[21] Appl. No.: 276,297

[22] Filed: Jun. 22, 1981

Related U.S. Application Data

[60] Continuation of Ser. No. 755,707, Dec. 30, 1976, abandoned, which is a division of Ser. No. 693,256, Jun. 7, 1976, Pat. No. 4,042,533.

[51] Int. Cl.$^3$ ............... C07C 51/25; C07C 57/055
[52] U.S. Cl. .................... 562/534; 252/435; 252/437; 252/464; 252/467; 252/468; 252/469; 252/470; 260/346.75; 560/208; 562/535; 562/536
[58] Field of Search ............... 562/534, 535; 252/435, 252/437, 467, 468, 469, 470, 464

[56] References Cited

U.S. PATENT DOCUMENTS 3,875,220 4/1975 White et al. .................. 562/534
4,017,423 4/1977 White et al. .................. 562/534

FOREIGN PATENT DOCUMENTS 2550440 5/1976 Fed. Rep. of Germany ...... 562/534

*Primary Examiner*—Vivian Garner
*Attorney, Agent, or Firm*—David J. Untener; Herbert D. Knudsen; Larry W. Evans

[57] ABSTRACT

The present invention relates to a process for the production of unsaturated aliphatic acids and the catalyst therefor, by the vapor phase oxidation of the corresponding unsaturated aliphatic aldehydes with molecular oxygen, optionally in the presence of steam, in the presence of an oxidation catalyst consisting of the oxides of the elements molybdenum, vanadium, and tungsten, plus at least one of the oxides selected from the group consisting of rhenium, and titanium and optionally one or more of the oxides of the elements manganese, iron, copper, tin, aluminum, cobalt, nickel, phosphorus, zinc, bismuth, silver, cadmium, niobium, arsenic, chromium, the alkali and the alkaline earth elements.

2 Claims, No Drawings

PROCESS FOR PRODUCING UNSATURATED ALIPHATIC ACIDS

This patent application is a continuation of Ser. No. 755,707 filed Dec. 30, 1976, now abandoned, which is a divisional of patent application Ser. No. 693,256, filed June 7, 1976, now U.S. Pat. No. 4,042,533.

BACKGROUND OF THE INVENTION

Catalyst compositions similar to those of the present invention are known for the oxidation of acrolein to acrylic acid. For example, the disclosure in U.S. Pat. No. 3,567,773 shows catalyst compositions containing the elements of molybdenum, vanadium and tungsten; German Pat. No. 2,456,100 discloses catalysts having the composition of molybdenum, vanadium and tungsten in combination with such elements as copper, cobalt and iron; and Belgian Pat. No. 773,851 discloses the catalyst composition antimony, molybdenum, vanadium and tungsten and which may also contain titanium among other elements.

THE INVENTION

The present invention relates to an improved process for producing olefinically unsaturated carboxylic acids from the corresponding unsaturated aldehydes and to the catalyst composition utilized therefor. More specifically, the present invention relates to a vapor phase process for producing acrylic acid or methacrylic acid from acrolein and methacrolein, respectively, by oxidation of the unsaturated aldehydes with molecular oxygen, optionally in the presence of steam, and in the presence of an oxidation catalyst having the empirical formula:

$$Mo_aV_bW_cX_dY_eO_f$$

wherein X is one or more of the elements selected from the group consisting of rhenium and titanium; and
Y is one or more of the elements selected from the group consisting of manganese, iron, copper, tin, zinc, aluminum, cobalt, nickel, phosphorus, cadmium, bismuth, silver, niobium, arsenic, chromium, alkali and alkaline earth elements, and
wherein the number of atoms of each element present is represented by a through f,
wherein a is a number from 6 to 18;
b is a number from 0.1 to 10;
c is a number from 0.1 to 6;
d is a number from 0.01 to 5;
e is a number from 0 to 5; and
f is a number that satisfies the valence requirements of the other elements present.

Preferred catalysts are those wherein a is between 9 and 15; b is between 0.5 and 5; c is between 0.5 and 3; d is between 0.05 and 1; and e is between 0 and 1. The elements are present in these catalytic composition in the form of their oxides or oxide complexes.

In addition to the active catalytic ingredients, the catalysts of the invention may contain a support material. Suitable support materials include silica, alumina, zirconia, silicon carbide, boron phosphate and the like. A preferred support material is Alundum.

The catalysts of this invention are highly effective for oxidation reactions such as the oxidation of butadiene to maleic anhydride and the oxidative esterification of unsaturated aldehydes to the corresponding unsaturated ester. Preferred among these oxidative reactions is the production of unsaturated acids from the corresponding unsaturated aldehyde, and more specifically the catalysts of the invention are capable of very selectively oxidizing acrolein to acrylic acid at low temperatures with little or no acetic acid production.

The oxidation of unsaturated aldehydes to obtain the corresponding acid is well known in the art. Basically, the invention, will respect to the process, is the use of the new catalyst within the parameters of the known art process.

The known process involves the contacting of the unsaturated aldehyde with molecular oxygen in the presence of steam at a temperature of about 200° to about 500° C. The ratio of the reactants may vary widely, with molar ratios of molecular oxygen to aldehyde of about 0.5 to about 5 normally being employed. Molecular oxygen is most conveniently added as air. The amount of steam may vary widely from the small amount generated in the reaction to 20 or more moles of steam per mole of aldehyde. In the preferred practice of the invention, about 1 to about 10 moles of steam are added to the reactant feed.

The reaction may be conducted in a fixed-bed or fluid-bed reactor or forms thereof, using atmospheric, superatmospheric or subatmospheric pressure. The apparent contact time may vary considerably, with contact times of a fraction of a second to 20 seconds or more normally being employed.

As noted above, catalysts very similar to the catalysts of the invention are known, see for example U.S. Pat. No. 3,567,773, and thus catalysts of this general type can readily be prepared by persons of ordinary skill in the art.

Normally, the catalysts of the invention are prepared by mixing the catalyst ingredients in the proper proportions in an aqueous mixture, drying the resulting aqueous slurry and calcining the product. The ingredients going into the preparation of the catalysts can be the oxides, halides, nitrates, acetates, or other salts of the particular compound added. If a support is used, the material comprising the support is usually incorporated into the catalyst along with the other ingredients. After the catalyst ingredients have been combined to form an aqueous slurry, the slurry is evaporated to dryness, and the dried solid obtained is heated in the presence of air at temperatures between about 200° and 600° C. This calcination can take place outside of the catalytic reactor or an in situ activation can be utilized.

There are a number of preparations that can be used to make desirable catalysts of the invention. A preparation used in the examples is shown in the Specific Embodiments; but it is not to be construed that the method of preparation is limited to the preparation described.

SPECIFIC EMBODIMENTS

Catalyst Preparation

The catalyst of Comparative Example A and the catalysts of Examples 1 and 2 which are representative of the present invention were prepared according to the following procedure.

COMPARATIVE EXAMPLE A

Catalyst $Mo_{12}V_3W_{1.2}O_{47.1}$

To 250 cc of hot distilled water was added 6.16 g of ammonium metavanadate. After this reagent was dissolved with heating and stirring, 5.84 g of ammonium metatungstate and 37.21 g of ammonium heptamolybdate were added and readily dissolved. The solution was evaporated to near dryness with continual heating and stirring, and the contents were then placed in a drying oven at approximately 120° C. for 16 hours. The dried material was crushed and ground to pass through a 50 mesh screen. A sufficient amount of powder was employed to coat 3/16" Alundum spheres to achieve a twenty weight percent coating on the spheres. The coated spheres were then dried at 120° C. for three hours and then activated by heat treating at 370° C. for two hours.

EXAMPLE 1

Catalyst $Mo_{12}V_3W_{1.2}Ti_{0.5}O_{48.1}$

The procedure of Comparative Example A was repeated using the same quantities of the same reagents, followed by the addition of 5.22 g of a twenty percent solution of titanous chloride, and the catalyst completed as described.

EXAMPLE 2

Catalyst $Mo_{12}V_3W_{1.2}Re_{0.2}O_{47.8}$

The procedure of Comparative Example A was repeated using the same quantities of the same reagents, followed by the addition of 0.942 g of ammonium perrhenate, and the catalyst completed as described.

The catalysts prepared above were placed in a fixed-bed reactor constructed of 1.0 cm.-inside diameter stainless steel tubing having a reaction zone of 20 c.c. The reactor was heated in a split block furnace. The reactor was fed with a mixture of acrolein/air/nitrogen/steam in the molar ratio of 1/8.5/2.5/6. The reaction was conducted at atmospheric pressure, and an apparent contact time was two seconds. The temperatures of the surrounding block employed in the reactions are given in Table I, and the results given in the Table are in terms of the following definitions:

$$\text{Percent Conversion} = \frac{\text{Moles of acrolein reacted} \times 100}{\text{Moles of acrolein fed}}$$

$$\text{Percent Single Pass Yield} = \frac{\text{Moles of product recovered} \times 100}{\text{Moles of acrolein fed}}$$

$$\text{Percent Selectivity} = \frac{\text{Moles of acrylic acid recovered} \times 100}{\text{Moles of acrolein reacted}}$$

The improved conversions of acrolein to acrylic acid obtained with the catalyst compositions of the present invention are readily apparent by the direct comparison of Examples 1 and 2 with Comparative Example A which represents a catalyst composition of the prior art.

In the same manner as shown by the examples above, other catalysts of the invention containing different amounts of rhenium and titanium and different optional elements, such as iron, zinc, aluminum, chromium, and the like are used to produce acrylic acid.

Also using the catalysts of the present invention, maleic anhydride, methacrylic acid or acrylates are produced by known oxidation reactions.

TABLE I

| | | Oxidation of Acrolein to Acrylic Acid | | | |
|---|---|---|---|---|---|
| Example No. | Catalyst Composition[1] | Reaction Temp., °C. | % Conv. of Acrolein | [Corrected[2] % Single Pass Yield of] Acrylic Acid | Acetic Acid | % Selec. to Acrylic Acid |
| Comp. A | $Mo_{12}V_3W_{1.2}O_{47.1}$ | 318 | 98.1 | 81.4 | 2.8 | 83.0 |
| 1 | $Mo_{12}V_3W_{1.2}Ti_{0.5}O_{48.1}$ | 293 | 99.3 | 93.4 | 1.1 | 94.0 |
| 2 | $Mo_{12}V_3W_{1.2}Re_{0.2}O_{47.8}$ | 302 | 97.1 | 87.0 | 1.9 | 89.6 |

[1]20% active catalyst component coated on 3/16" Alundum spheres.
[2]Corrected to 100% carbon balance.

We claim:

1. The process for the production of acrylic acid or methacrylic acid by the vapor phase oxidation of acrolein and methacrolein, respectively, with molecular oxygen optionally in the presence of steam at a temperature of about 200° to about 500° C. employing a catalyst having the empirical formula $$Mo_a V_b W_c X_d Y_e O_f$$

wherein X is rhenium; and
Y is one or more of the elements selected from the group consisting of manganese, iron, copper, tin, zinc, aluminum, cobalt, nickel, phosphorus, cadmium, bismuth, silver, niobium, arsenic, chromium, the alkali and the alkaline earth elements, and
wherein the number of atoms of each element present is represented by a through f,
wherein a is a number from 6 to 18;
b is a number from 0.1 to 10;
c is a number from 0.1 to 6;
d is a number from 0.01 to 5;
e is a number from 0 to 5; and
f is a number that satisfies the valence requirements of the other elements present.

2. The process in claim 1 wherein in the empirical formula a=9 to 15; b=0.5 to 5; c=0.5 to 3; d=0.05 to 1; e=0 to 1; and f is a number that satisfies the valence requirements of the other elements present.

* * * * *